United States Patent
Mathur et al.

(10) Patent No.: US 9,567,270 B1
(45) Date of Patent: Feb. 14, 2017

(54) PROCESS FOR PRODUCING EXO-TETRAHYDRODICYCLOPENTADIENE

(71) Applicant: Johann Haltermann Limited, Houston, TX (US)

(72) Inventors: Indresh Mathur, Sugar Land, TX (US); Karel Johannes Kriel, Houston, TX (US); Edward Hirohito Yonemoto, Pearland, TX (US)

(73) Assignee: Johann Haltermann Limited, Houston, TX (US)

( * ) Notice: Subject to any disclaimer, the term of this patent is extended or adjusted under 35 U.S.C. 154(b) by 0 days.

(21) Appl. No.: 15/056,448

(22) Filed: Feb. 29, 2016

(51) Int. Cl.
  *C07C 5/22* (2006.01)
(52) U.S. Cl.
  CPC ......... *C07C 5/2253* (2013.01); *C07C 2527/10* (2013.01)
(58) Field of Classification Search
  None
  See application file for complete search history.

(56) References Cited

U.S. PATENT DOCUMENTS

| | | |
|---|---|---|
| 3,167,595 A | 1/1965 | Heywood et al. |
| 3,235,614 A | 2/1966 | Fritz et al. |
| 3,381,046 A | 4/1968 | Cohen et al. |
| 3,725,498 A * | 4/1973 | Brennan ................ B01J 27/125 502/169 |
| 3,833,678 A | 9/1974 | Brennan |
| 4,086,284 A | 4/1978 | Schneider et al. |
| 4,107,223 A | 8/1978 | Schneider et al. |
| 4,270,014 A | 5/1981 | Norton et al. |
| 4,604,490 A | 8/1986 | Yuasa et al. |
| 4,762,092 A | 8/1988 | Yuasa et al. |
| 4,804,795 A | 2/1989 | Yuasa et al. |
| 7,488,860 B2 | 2/2009 | Huang et al. |
| 8,017,821 B2 | 9/2011 | Huang et al. |
| 8,450,544 B2 | 5/2013 | Tsao et al. |

* cited by examiner

*Primary Examiner* — In Suk Bullock
*Assistant Examiner* — Philip Louie
(74) *Attorney, Agent, or Firm* — Butzel Long

(57) ABSTRACT

A process for isomerizing endo-hydrogenated dicyclopentadiene to form the corresponding exo-isomer using a stable, pumpable liquid aluminum halide catalyst which includes steps of providing a first solution containing a hydrogenated dicyclopentadiene compound that is dissolved in a hydrocarbon solvent, adding a cosolvent to the first solution to form a second solution, adding an aluminum halide to the second solution, and isomerizing the hydrogenated dicyclopentadiene compound in the presence of dissolved aluminum halide which acts as a catalyst to produce the corresponding exo-isomer.

18 Claims, 3 Drawing Sheets

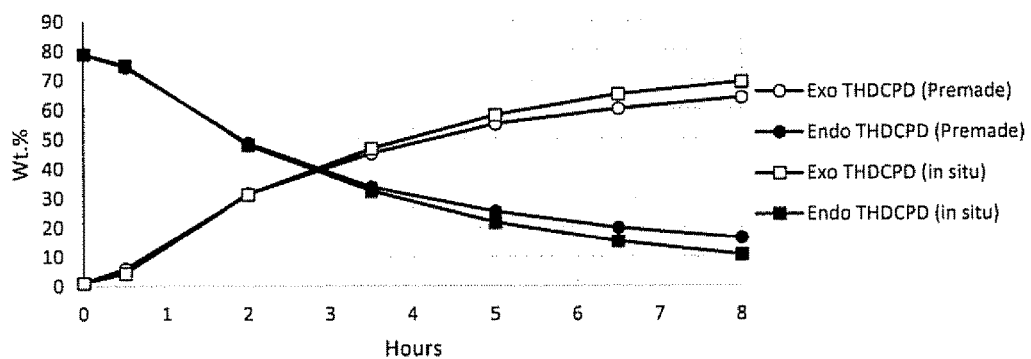
Fig. 1. Premade catalyst addition vs in situ catalyst addition
1.4 mol AlCl$_3$ per mol C4ME
(~0.9 lbs AlCl$_3$ per 100 lbs endo feed)
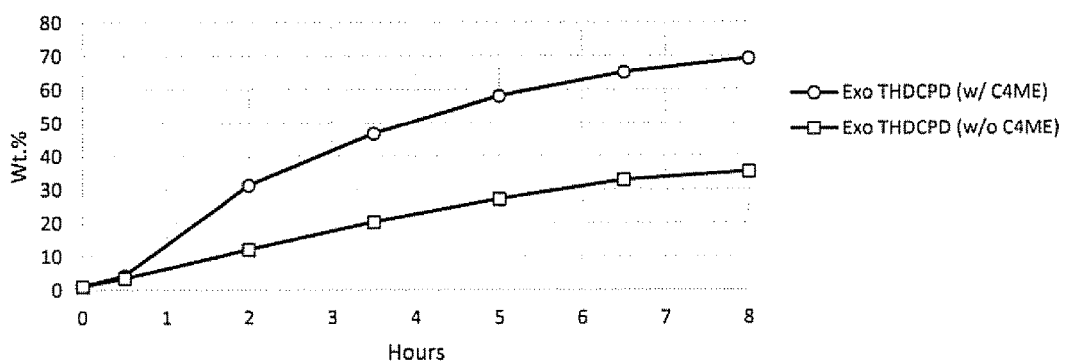
Fig. 2. Showing ~0.9 lbs AlCl$_3$ per 100 lbs endo feed with and without C4ME Fig. 3. Impact of Low and High Bromine Index feed
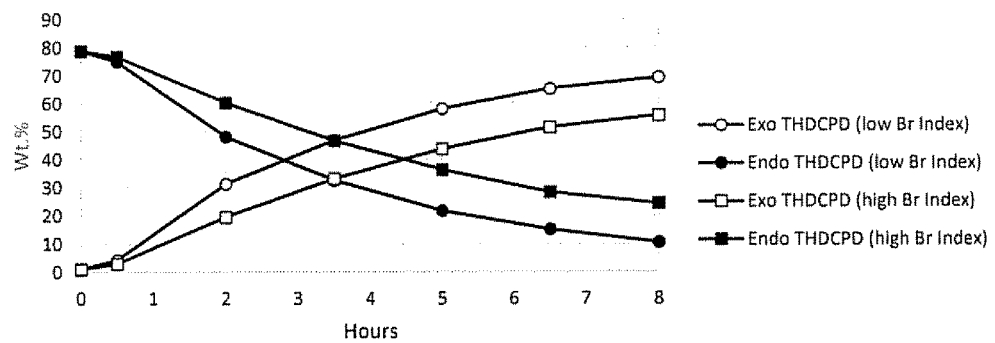
Fig. 4. In situ addition of 1.4 and 1.8 moles $AlCl_3$ per mole C4ME (~0.9 lb. and ~1.2 lb $AlCl_3$ per 100 lb endo feed)
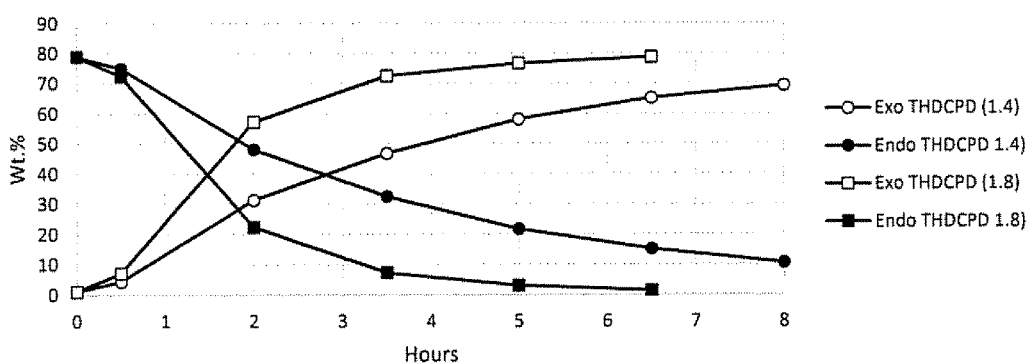

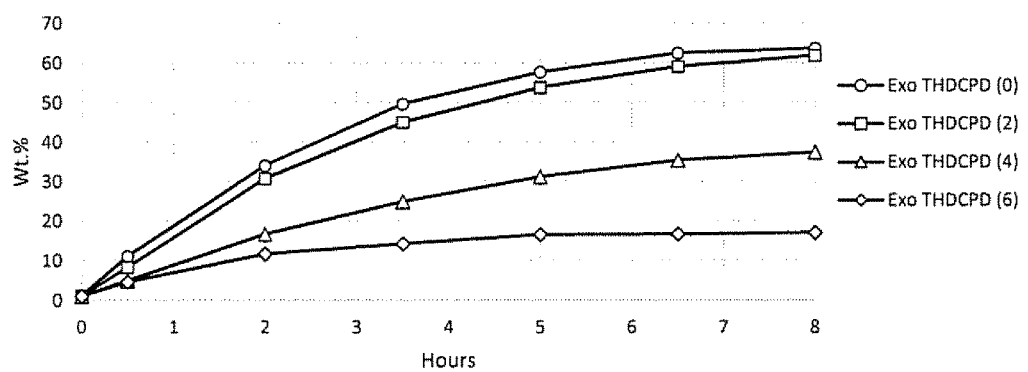
Fig. 5 The activity premade aluminum chloride/C4ME complex after 0, 2, 4 and 6 weeks

PROCESS FOR PRODUCING EXO-TETRAHYDRODICYCLOPENTADIENE

CROSS-REFERENCE TO RELATED APPLICATIONS

Not Applicable.

FIELD OF THE DISCLOSURE

This disclosure relates to the production of exo-tetrahydrodicyclopentadiene compounds, and more specifically to a liquid phase acid catalyst system for isomerization of endo-hydrogenated dicyclopentadiene compounds.

BACKGROUND OF THE DISCLOSURE

Exo-tetrahydrodicyclopentadiene (exo-THDCPD) is a high density liquid missile fuel. This single component fuel, also known as JP-10 is obtained by hydrogenation of dicyclopentadiene (DCPD) to endo tetrahydro-dicyclopentadiene (endo-THDCPD) and the isomerization of endo-THDCPD to the exo-THDCPD isomer. The exo-THDCPD isomer has a melting point of −79° C. and is the main component of JP-10. The endo-THDCPD has a freezing point of +77° C. and is therefore not a good candidate for high density liquid fuel.

In the manufacture of exo-THDCPD, the hydrogenation of the DCPD is fairly straight forward. The feed of DCPD, which is mostly the endo-isomer, is kept in solution by dissolution into a paraffinic solvent (i.e., mostly linear paraffin of C6-C9). The hydrotreated stream, which is mostly an endo-isomer, is then isomerized to the exo-isomer. The finished product exo-THDCPD of greater than 98% purity is then produced by distillation of the isomerized stream.

In the manufacture of exo-THDCPD, isomerization of the endo-THDCPD to exo-THDCPD is the most difficult processing step. Various acidic catalysts have been used to facilitate the isomerization reaction.

In the prior art. JP-10 is prepared by first completely hydrogenating extra-high purity cyclopentadiene (CPD) dimer, namely dicyclopentadiene (DCPD, freezing point of 33.6° C.), as a precursor to yield the solid endo-isomer of the hydrogenated derivative, namely endo-THDCPD (freezing point of 77° C.), wherein the hydrogenation of DCPD is carried out in two stages. In the first stage, the dihydro derivative, namely dihydrodicyclopentadiene (DHDCPD, freezing point of 51° C.) was obtained by selective hydrogenation of DCPD in the presence of nickel or palladium catalyst at a temperature of 50-120° C. In the second stage, the solid endo-THDCPD (freezing point of 77° C.) was obtained by hydrogenation of DHDCPD in the presence of metal catalyst at a temperature of 130-220° C. Finally, the solid endo-THDCPD is isomerized to the liquid exo-THDCPD, namely JP-10 (freezing point <−79° C.), in an amount of more than 98.5% of the total product weight in the presence of an acidic catalyst. JP-10 is very expensive because it is obtained by chemical synthesis from extra-high purity DCPD using a batch reactor (referring to U.S. Pat. Nos. 3,381,046; 4,086,284; 4,107,223 and 4,270,014).

Isomerization of endo-hydrogenated dicyclopentadiene compounds to form exo-isomer have generally involved the use of solid acid catalysts that are either supported in a fixed bed type reactor or suspended in a slurry type reactor. Because suspended solid catalysts are difficult to handle, it is desirable to employ a liquid catalyst.

SUMMARY OF THE DISCLOSURE

A process for isomerizing endo-hydrogenated dicyclopentadiene to form exo-isomer using a stable pumpable liquid aluminum halide catalyst is disclosed. The process involves providing a first solution containing a hydrogenated dicyclopentadiene compound that is dissolved in a hydrocarbon solvent, adding a cosolvent to the first solution to form a second solution, the cosolvent selected to enhance dissolution of an aluminum halide catalyst, adding an aluminum halide catalyst to the second solution, and isomerizing dissolved endo-hydrogenated dicyclopentadiene compound in the presence of dissolved aluminum halide catalyst to produce the corresponding exo-isomer.

Other features and advantages of the present disclosure will become readily appreciated as the same becomes better understood after reading the following description.

BRIEF DESCRIPTION OF THE DRAWINGS

FIG. 1 is a graph of the isomerization rate when a catalyst-cosolvent complex is added to a solution containing endo-THDCPD compared with the isomerization rate when the cosolvent and catalyst are added sequentially.

FIG. 2 is a graph comparing isomerization rate with and without cosolvent.

FIG. 3 is a graph showing the effect of Bromine Index of the feed on the isomerization.

FIG. 4 is a graph comparing the progress of isomerization using a mole ratio of $AlCl_3$ to methyl butanoate of 1.4 to that using a ratio of 1.8.

FIG. 5 is a graph showing the effect that aging of a premade aluminum chloride/methyl butanoate complex has on isomerization rate.

DETAILED DESCRIPTION

The disclosed process employs a cosolvent that enhances dissolution of aluminum halide in a liquid phase reaction system to provide a relatively simple and economical process for producing exo-hydrogenated dicyclopentadiene compounds from the corresponding endo-isomer. The process also advantageously involves first adding the cosolvent to a solution containing the endo-hydrogenated dicyclopentadiene compound(s), and subsequently adding the aluminum halide catalysts. This sequence allows higher ratios of aluminum halide to cosolvent, facilitating more efficient utilization of the aluminum halide catalyst.

The endo-hydrogenated dicyclopentadiene compound can be a completely hydrogenated endo-dicyclopentadiene, or a completely hydrogenated alkyl-substituted endo-dicyclopentadiene. Examples include endo-tetrahydrodicyclopentadiene, and endo-tetrahydrodimethyl dicyclopentadiene.

The endo-hydrogenated dicyclopentadiene can be isomerized in accordance with this disclosure by providing a first solution containing an endo-hydrogenated dicyclopentadiene compound that is dissolved in a hydrocarbon solvent. The hydrocarbon solvent can comprise linear and branched paraffins, naphthenes (cyclic paraffins), or combinations of these hydrocarbons. In certain embodiments the solvent is comprised predominately of linear paraffins, e.g., at least 50%, 60%, 70%, 80% or 90% linear paraffins by weight.

Suitable cosolvents include a variety of halogenated solvents, such as methylene chloride, dichloromethane, trichloroethane, tetrachloroethylene, carbon tetrachloride, etc. However, due to the difficulty of meeting environmental, health, and safety regulations, it is desirable to use a cosolvent, or aluminum halide solubility enhancer, that is not halogenated.

It has been found that non-halogenated cosolvents that can be advantageously used in the disclosed isomerization process include linear alkyl esters of a carboxylic acid, such as those having from five to nine carbon atoms. Suitable alkyl esters of a carboxylic acid include methyl esters, such as those having from 5 to 9 carbon atoms, e.g., methyl butanoate (methyl butyrate), methyl pentanoate (methyl valerate), methyl hexanoate (methyl caproate), and methyl octanoate (methyl caprylate). Other examples include propyl propanoate (propyl propionate), and ethyl butanoate (ethyl butyrate).

Suitable aluminum halides include aluminum chloride (empirical formula $AlCl_3$), and aluminum bromide.

The aluminum halide is added slowly after the cosolvent (or aluminum halide solubility enhancer) is added. This allows a higher proportion (weight ratio) of aluminum halide to solvent and better process efficiency and economy. For example, it is possible to add and completely dissolve more aluminum chloride in proportion to the alkyl ester of a carboxylic acid when the aluminum chloride is slowly added after the ester is added. For example, a molar ratio of aluminum chloride to alkyl ester of a carboxylic acid can be greater than 1.4:1, 1.6:1, 1.7:1, or 1.8:1, allowing higher and more effective utilization of the aluminum chloride catalyst. The catalyst is added in an amount that is effective to catalyze the isomerization reaction, e.g., typically about 0.5% to 2% of the reactor system (i.e., solvent, cosolvent, reactant and catalyst).

The following non-limiting examples illustrate the processes disclosed herein.

Isomerization of Endo THDCPD to Exo THDCPD

Feed for Isomerization Reaction. The feed for evaluation of isomerization was the hydrogenated product of dicyclopentadiene (DUD) and heptane prepared in the hydrogenation reactor.

| Feed for Isomerization | |
|---|---|
| Appearance | Clear |
| Water (wt. % by K.F.) | 0.008 |
| Acidity (wt. % as HAe) | 0.005 |
| Chloride (ppm) | <10 |
| Bromine Index | 7 |
| Lights | 0.04 |
| n-Hexane | 0.56 |
| 2-Methyl hexane | 0.00 |
| 3-Methyl hexane | 0.02 |
| n-Heptane | 17.60 |
| C9/C10 Codimers | 0.53 |
| exo-THDCPD | 1.09 |
| endo-THDCPD | 78.41 |
| Intermediates | 0.24 |
| Heavies | 1.51 |

Hexane, heptane, aluminum chloride and methyl butanoate (C4ME) were used as received from Aldrich Chemical and other suppliers.

Various Lewis acid catalysts and ionic liquids were evaluated for the isomerization reaction catalysis in the laboratory and were found to be not as effective as aluminum chloride. The initial isomerization process to convert endo THDCPD to exo THDCPD used methylene chloride to solvate the powdered aluminum chloride catalyst necessary for the isomerization process. However, the use of any amount of methylene chloride would be prohibitive in plant operations due to Environmental Health and Safety (EH&S) considerations. We have determined that an alternate method of choice was the use of methyl butanoate (C4ME) to convert powdered aluminum chloride into a phase separating liquid. Aluminum chloride can be dissolved in C4ME forming a pumpable liquid aluminum chloride/ester complex which was described in U.S. Pat. No. 3,833,678. The aluminum chloride/ester complex is a 1:1 molar complex generating a liquid phase in which additional aluminum chloride can be dissolved into solution. This additional aluminum chloride dissolved in the 1:1 molar complex of C4ME and aluminum chloride is the active aluminum chloride in a pumpable liquid state that functions in the catalysis of endo-THDCPD to exo-THDCPD. It is already known from prior art that only 1.1 to 1.4 moles of aluminum chloride can be dissolved per mole of C4ME. The process of this invention describes how greater than 1.4 molar ratios of aluminum chloride in C4ME can be achieved in order to facilitate the isomerization reaction.

The formation of the aluminum chloride/C4ME complex was very exothermic. This was carefully performed by slowly adding aluminum chloride powder to C4ME in a 1.0 to 1.4 molar ratio with stirring in a cold water bath. Once the beige-amber liquid complex solution was prepared, it was stored under dry nitrogen. As will be apparent, this invention addresses the issue of intense heat evolution when aluminum chloride is complexed with esters like C4ME.

The various small scale experiments were performed at room temperature (~23° C.) with stirring at 500 rpm using a Teflon magnetic stir bar. The reaction flask was a 100 ml round bottom flask with a cap to prevent moisture from entering the reaction mixture. The aluminum catalyst deactivates in the presence of water. The hydrogenated feed stock of ~20% n-heptane and ~80% endo THDCPD with a low Bromine Index value of 7 was used to evaluate endo to exo isomerization catalytic conversion.

The activity of the premade beige-amber liquid aluminum chloride/C4ME complex was evaluated by the addition of 1.4 wt. % of this solution to the hydrogenated reactor feed stock of endo THDCPD. The liquid aluminum chloride/C4ME complex formed small droplets swirling in the reaction mixture. The beige-amber liquid complex became dark orange in color forming the "red oil" phase which was also observed when methylene chloride was used as a catalyst solvent.

In order to better dissipate the heat of formation of the aluminum chloride/C4ME complex, methyl butanoate (C4ME) was added and diluted into the hydrogenated reactor product. The same amount of reactants were used as in the initial test above except that the addition order was changed. The reaction mixture was prepared by adding 0.5 wt. % C4ME to the hydrogenated reactor product. Then 0.9 wt. % aluminum chloride powder (IA molar ratio) was added last with stirring. The aluminum chloride powder was initially a suspended powder which started to agglomerate and stick to the sides of the round bottom reaction flask after ~5 minutes. After ~30 minutes, the catalyst mixture was a yellow oil with some solid aluminum chloride powder. The suspension of solid aluminum chloride powder completely dissolved into the dark yellow oil droplets in ~60 minutes. The oil was dark orange at the end of the isomerization reaction and phase separated from the bulk of the reaction mixture once stirring was stopped.

The plot in FIG. 1 shows the progress of the isomerization reaction using the same amounts of C4ME and aluminum chloride powder described above comparing the two different catalyst addition methods.

The two isomerization rates are essentially the same indicating that there is not a significant difference in which the order of reactants were added.

Advantages of Using Catalyst Co-Solvent

For comparison, the importance in the use of C4ME can be seen when the isomerization reaction was performed without C4ME. In essence, 100% active aluminum chloride was added to the reaction mixture as none of the catalyst is consumed in the formation of the aluminum chloride/C4ME complex. That is ~0.9 wt. active catalyst as compared to ~0.25 wt % active catalyst in the presence of C4ME.

The aluminum chloride powder was added to the hydrogenated reaction mixture with stirring. The aluminum chloride powder was initially a beige suspension and after ~30 minutes agglomerated to fine dark yellow particulates stirring in solution. After ~60 minutes, the particulates became dark orange and at ~300 minutes the particulates became big enough and started sticking to the walls of the round bottom reaction flask. The rate of isomerization was very slow and the formation of the "red oil" was not observed. The plot (FIG. 2) shows the progress of the isomerization reaction with and without C4ME.

Impact of Degree of Hydrogenation on Isomerization Process

Another factor influencing the isomerization reaction is the degree of hydrogenation of the feed for the isomerization process. Bromine Index, which is the measure of the degree of unsaturation of the hydrogenated reactor product feeding the isomerization process. The isomerization of hydrogenated stream with a Bromine Index of 7 was compared to a sample with a Bromine Index of 31. The reaction mixture was prepared by adding 0.5 wt. % C4ME to the "low" and "high" Bromine Index hydrogenated reactor product. Then 0.9 wt. % aluminum chloride powder was added with stirring. The plot in FIG. 3 shows the progress of the isomerization reaction.

The two samples looked similar other than that the aluminum chloride/C4ME complex oily phase was darker orange in color for the "high" Bromine Index sample than for the "low" Bromine Index sample. The unsaturated compounds contributing to the Bromine Index appear to polymerize and also consume active aluminum chloride which then was incorporated into the red oil phase. Therefore, the hydrogenation process should produce a hydrogenated feed stock of ~20% n-heptane and ~80% endo THDCPD with a Bromine Index of 10 or less for the most efficient use of aluminum chloride.

Effect of Order of Addition of Catalyst and Cosolvent

Premixing the catalyst C4ME solvent with the hydrogenated endo THDCPD and then (in situ) adding the aluminum chloride catalyst allows more catalyst to be incorporated into a liquid phase than using the premade aluminum chloride/C4ME complex and adding it to the isomerization reactor. When an aluminum chloride/C4ME complex is premade, there is a saturation point at ~1.4 molar excess of aluminum chloride with respect to C4ME. However, it was found that ~1.8 molar excess of aluminum chloride with respect to C4ME could be added when aluminum chloride was added to the isomerization reaction when the catalyst solvent was already mixed with the reactants for the isomerization process. The reaction mixture was prepared by the addition of ~0.5 wt. % C4ME to the feed stock of ~20% n-heptane and ~80% endo THDCPD. Aluminum chloride powder was then added to the diluted ester in the isomerization reaction mixture with stirring. The amount of aluminum chloride was ~1.2 wt. % of the batch reaction which is in a 1.0 to 1.8 molar ratio of aluminum chloride catalyst to C4ME. The amount of aluminum chloride forming the complex with the ester was ~0.7 wt. %, leaving ~0.5 wt. % as active aluminum chloride. The suspension of solid aluminum chloride powder completely dissolved into the dark yellow oil droplets in ~~90 minutes. The oily complex was dark orange in color at the end of the isomerization reaction at ~400 minutes and phase separated from the bulk of the reaction mixture once stirring was stopped. The plot in FIG. 4 shows the progress of the isomerization reaction with the aluminum chloride complex made in situ at the 1.4 and 1.8 molar ratio. This respectively corresponds to ~0.25 and ~0.5 wt. % active aluminum chloride.

The premade aluminum chloride/C4ME complex oil has a saturation point at ~1.4 molar excess of aluminum chloride with respect to C4ME. In order to obtain an equivalent amount of active (dissolved) aluminum chloride, twice the amount of premade aluminum chloride/C4ME complex oil would be required. The addition of 2.8 wt. % premade oil would contribute ~0.5 wt. % active aluminum chloride. This amount of active aluminum chloride corresponds to 1.8 molar ratio with respect to C4ME when prepared in situ.

The use of the premade aluminum chloride/C4ME complex oil would require the use of more C4ME and aluminum chloride as most of the volume of the liquid catalyst mixture is the form of the inactive aluminum chloride/C4ME complex. U.S. Pat. No. 3,833,678 also indicated that the aluminum chloride complex mixture decreases in catalytic activity and increases in viscosity over time. This was evaluated using the aluminum chloride/C4ME complex oil prepared and stored in a 40 ml septa vial. The isomerization activity was monitored in two week intervals. The plot FIG. 5 shows the activity of the isomerization reaction over time using the premade aluminum chloride/C4ME complex oil. The effect of using the premade aluminum chloride/C4ME complex are apparent from the data presented in this graph.

Recycle of the AlCl3 Complex Oil

A method to recycle the AlCl3 Complex oil and maintain relatively quick reaction rates is the addition of additional aluminum chloride into the successive batches. The initial batch had 0.5 wt. % C4ME in the ~20% n-heptane and ~80% endoTHDCPD feed stock. Then 0.9 wt. % aluminum chloride powder (1.4 molar ratio) was added with stirring. The second batch was started by decanting the upper crude exoTHDCPD from the AlCl3 Complex oil and then adding an equal amount of fresh feed stock without C4ME. An additional ~0.3 wt. % aluminum chloride was then added with stirring. Once the second batch was complete, the upper layer was again decanted and replaced with fresh feed stock with additional aluminum chloride for the third batch. The additional aluminum chloride dissolved into the AlCl3 Complex oil in each batch. In this matter the bulk of the AlCl3 Complex oil is recycled between a limited number of batches.

Finished Product JP-10

Finished product JP-10 (exo-tetrahydrodicyclopentadiene) (exo-THDCPD) was produced in laboratory with the aluminum chloride/methyl butanoate complex oil prepared in situ during the isomerization reaction converting endo THDCPD to exo THDCPD. Commercially available particle size grades of aluminum chloride and very fine chemically pure aluminium chloride from Aldrich gave similar results. Various wash procedures for in situ neutralizing or washing and removing spent aluminum chloride from the reactor product were evaluated. The resulting crude reaction mixture was distilled to produce the finished product exo-THDCPD (JP-10). The results are given below:

|  | Trial 1 | Trial 2 | F.P. Specs. |
| --- | --- | --- | --- |
| Lights | 0.00 | 0.00 | |
| C9/C10 codimers | 0.01 | 0.20 | |
| trans-Decalin | 0.18 | 0.11 | |
| exo-THDCPD | 98.70 | 99.06 | 98.5 min. |
| Intermediates | 0.02 | 0.04 | |
| Adamantane | 0.06 | 0.13 | |
| endo-THDCPD | 1.03 | 0.46 | |

The described embodiments are not limiting. Various modifications are considered within the purview and scope of the appended claims.

What is claimed is:

1. A process for isomerization of an endo-hydrogenated dicyclopentadiene compound to produce a corresponding exo-hydrogenated dicyclopentadiene compound, comprising:
    providing a first solution containing an endo-hydrogenated dicyclopentadiene compound dissolved in a hydrocarbon solvent;
    adding a cosolvent to the first solution to form a second solution;
    adding an aluminum halide catalyst to the second solution; and
    isomerizing dissolved endo-hydrogenated dicyclopentadiene compound in the presence of dissolved aluminum halide catalyst to produce exo-hydrogenated dicyclopentadiene compounds, wherein the cosolvent is a linear alkyl ester of a carboxylic acid.

2. The process of claim 1, wherein the endo-hydrogenated dicyclopentadiene compound is endo-tetrahydrodicyclopentadiene.

3. The process of claim 1, wherein the endo-hydrogenated dicyclopentadiene compound is endo-tetrahydromonomethyl dicyclopentadiene or endo-tetrahydrodimethyl dicyclopentadiene.

4. The process of claim 1, wherein the alkyl ester of a carboxylic acid has from five to nine carbon atoms.

5. The process of claim 1, wherein the alkyl ester of a carboxylic acid is a methyl ester of a carboxylic acid.

6. The process of claim 5, wherein the alkyl ester of a carboxylic acid has from five to nine carbon atoms.

7. The process of claim 1, wherein the alkyl ester of a carboxylic acid is methyl butanoate.

8. The process of claim 1, wherein the alkyl ester of a carboxylic acid is selected from propyl propanoate and ethyl butanoate.

9. The process of claim 1, wherein the hydrocarbon solvent is comprised of at least 50 percent linear paraffins by weight.

10. The process of claim 1, wherein the aluminum halide is aluminum chloride.

11. The process of claim 10, wherein a molar ratio of aluminum chloride to the alkyl ester of a carboxylic acid is greater than 1.4:1.

12. The process of claim 10, wherein a molar ratio of aluminum chloride to the alkyl ester of a carboxylic acid is greater than 1.6:1.

13. The process of claim 10, wherein a molar ratio of aluminum chloride to the alkyl ester of a carboxylic acid is greater than 1.7:1.

14. The process of claim 10, wherein a molar ratio of aluminum chloride to the alkyl ester of a carboxylic acid is up to 1.8:1.

15. The process of claim 1, wherein the first solution comprises a mixture of endo-hydrogenated dicyclopentadiene having a Bromine Index of 10 or less.

16. The process of claim 1, wherein the exo-hydrogenated dicyclopentadiene compounds partition into an upper liquid phase from the lower liquid phase containing the aluminum halide catalyst, and which further comprises decanting the upper liquid phase from the lower liquid phase, adding fresh endo-hydrogenated dicyclopentadiene to the lower liquid phase, optionally adding additional aluminum halide, and isomerizing the fresh endo-hydrogenated dicyclopentadiene.

17. The process of claim 16, wherein the steps of claim 16 are repeated one or more times.

18. A process for isomerization of an endo-hydrogenated dicyclopentadiene compound to produce a corresponding exo-hydrogenated dicyclopentadiene compound, comprising:
    (a) providing a liquid system comprising a hydrocarbon solvent, a cosolvent that enhances dissolution of an aluminum halide, and endo-hydrogenated dicyclopentadiene compound to form a solution;
    (b) adding an aluminum halide catalyst to the solution;
    (c) isomerizing the endo-hydrogenated dicyclopentadiene compound;
    (d) allowing product exo-hydrogenated dicyclopentadiene compounds to separate into an upper liquid phase;
    (e) decanting the upper liquid phase from a lower liquid phase containing the hydrocarbon solvent, the cosolvent and the aluminum halide catalyst;
    (f) adding fresh endo-hydrogenated dicyclopentadiene compound to the lower liquid phase, and optionally adding additional aluminum halide;
    (g) isomerizing the fresh endo-hydrogenated dicyclopentadiene compound; and
    (h) optionally repeating steps (d) through (g) one or more times, wherein the cosolvent is a linear alkyl ester of a carboxylic acid.

* * * * *